United States Patent
Sachdev et al.

(10) Patent No.: US 10,841,514 B2
(45) Date of Patent: Nov. 17, 2020

(54) ENDOSCOPY VIDEO FEATURE ENHANCEMENT PLATFORM

(71) Applicant: EndoVigilant, LLC, Millersville, MD (US)

(72) Inventors: Vineet Sachdev, Millersville, MD (US); Ravindra Kompella, Hyderabad (IN); Om P. Chaurasia, Mission Viejo, CA (US); H. David Helsley, Jr., Gilberts, IL (US)

(73) Assignee: EndoVigilant Inc, Millersville, MD (US)

( * ) Notice: Subject to any disclaimer, the term of this patent is extended or adjusted under 35 U.S.C. 154(b) by 0 days.

(21) Appl. No.: 16/359,822

(22) Filed: Mar. 20, 2019

(65) Prior Publication Data
US 2019/0297276 A1     Sep. 26, 2019

Related U.S. Application Data

(60) Provisional application No. 62/645,413, filed on Mar. 20, 2018.

(51) Int. Cl.
| | |
|---|---|
| *H04N 5/272* | (2006.01) |
| *G16H 30/40* | (2018.01) |
| *A61B 1/00* | (2006.01) |
| *G06T 7/12* | (2017.01) |
| *G10L 15/22* | (2006.01) |
| *G10L 15/00* | (2013.01) |
| *H04N 5/45* | (2011.01) |

(Continued)

(52) U.S. Cl.
CPC ......... *H04N 5/272* (2013.01); *A61B 1/00011* (2013.01); *A61B 1/00124* (2013.01); *G06T 7/0012* (2013.01); *G10L 15/22* (2013.01); *G10L 15/265* (2013.01); *G16H 30/40* (2018.01); *H04N 5/45* (2013.01); *H04N 7/01* (2013.01); *G06T 2207/10016* (2013.01); *G06T 2207/10068* (2013.01); *G06T 2207/20081* (2013.01); *G10L 2015/223* (2013.01)

(58) Field of Classification Search
None
See application file for complete search history.

(56) References Cited

U.S. PATENT DOCUMENTS 9,530,205 B2 * 12/2016 Kim .................. A61B 1/00009
9,741,116 B2    8/2017 Liang et al.
(Continued)

FOREIGN PATENT DOCUMENTS

WO    WO 2018/007139    1/2018

*Primary Examiner* — Edemio Navas, Jr.
(74) *Attorney, Agent, or Firm* — William H. Bollman (57) ABSTRACT

An endoscopy video feature enhancement platform (EVFEP) is connected to the output of any type endoscope system, and inputs and captures the output video. The video is visually augmented live with indicators of possible polyp detection and localization, polyp attributes, and procedure metrics, based on the collective learning of the output results of many different types of endoscopy systems on a large scale. An artificial intelligence model is trained on confirmed polyp detection previously determined by this and other EVFEP devices used with many different types of endoscope systems on a large scale. Augmented video, images and automatically generated short video clips of key procedure segments are passed to a reporting system, and supplemented with meta data.

11 Claims, 9 Drawing Sheets

(51) Int. Cl.
*H04N 7/01* (2006.01)
*G06T 7/00* (2017.01)
*G10L 15/26* (2006.01)

(56) References Cited

U.S. PATENT DOCUMENTS

| | | |
|---|---|---|
| 9,747,687 B2 | 8/2017 | Tajbakhsh et al. |
| 9,978,142 B2 * | 5/2018 | Chi ........................ G06T 7/0012 |
| 10,052,027 B2 | 8/2018 | Tajbakhsh et al. |
| 10,055,843 B2 * | 8/2018 | Tajbakhsh ............ A61B 5/4255 |
| 10,140,421 B1 * | 11/2018 | Bernard ................ G06F 40/247 |
| 2014/0375768 A1 * | 12/2014 | Tsuchiya ............ A61B 1/00011 |
| | | 348/45 |

* cited by examiner

ENDOSCOPY VIDEO FEATURE ENHANCEMENT PLATFORM

This application claims priority from U.S. Provisional No. 62/645,413 to "Endoscopy Video Feature Enhancement Platform Having Embedded Artificial Intelligence" filed Mar. 20, 2018, the entirety of which is explicitly incorporated herein by reference.

BACKGROUND OF THE INVENTION

1. Field of the Invention

The invention relates generally to medical technology. In particular, the invention relates to endoscopy equipment used for various endoscopy procedures including colonoscopy.

2. Background of Related Art

Increased and effective colorectal screening has resulted in a significant reduction in new incidence of colorectal cancer cases and associated deaths since 2001. But colorectal cancer still remains the third leading cause of cancer related deaths in the US. Colonoscopy or endoscopy of the colon is one of the most effective and widely used screening and intervention procedures for cancer.

The prevailing view is that the efficacy of the use of colorectal screening is not much better because of significant deviation and disparity in the visualization capabilities of different physicians, and disparity in their performance in detecting adenomas (pre-cancerous polyps).

Conventional endoscope systems are based on vendor-specific or proprietary hardware and software, resulting in a closed system.

The efficiency of endoscopy procedures is limited by the amount of time spent by physicians in documenting the procedure findings. Physicians document endoscopy procedures via manual entry into a separate procedure reporting system or an electronic medical record (EMR) system. Efficiency of course impacts the number of endoscopy procedures that can be performed by a physician on any given day, thereby impacting the total population that can be screened.

Endoscopy procedures are performed by gastroenterologists to detect, diagnose and treat various abnormalities including pre-cancerous polyps, ulcers, and inflammation of the digestive tract. Upper endoscopy focuses on the esophagus, stomach, and small intestines, whereas lower endoscopy or colonoscopy focuses on the lining of the large intestine (colon and rectum).

Figure 8:
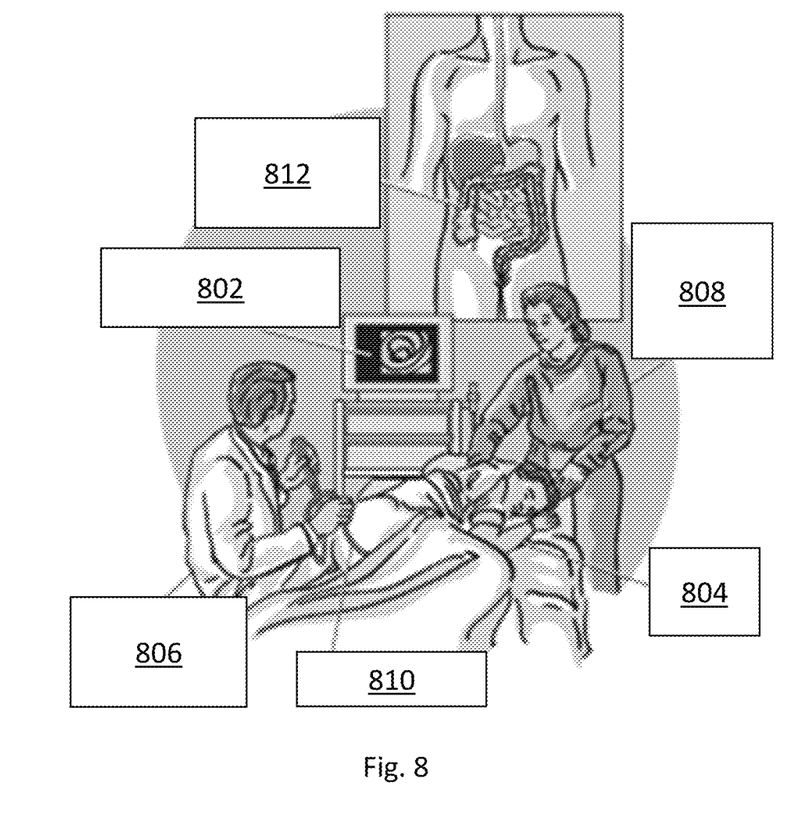
FIG. 8 shows a conventional endoscopy procedure.

FIG. 8 shows a conventional endoscopy procedure.

In particular, as shown in FIG. 8, a physician 806 performs a colonoscopy and a nurse 808 typically assists during the procedure. A conventional endoscopy procedure uses a colonoscope 810 to provide a live video monitor or screen 802 showing video images from inside the colon of digestive tract of a patient 804. The colonoscope 810 includes a thin, flexible tube with a light and camera at the tip 812 of the colonoscope 810.

As the endoscopy procedure proceeds, gastroenterologists and assisting technicians observe live video of the digestive tract from the endoscope camera on the large video monitor or screen 802. In some instances, especially in academic institutions, video recordings of these endoscopy procedures are made for later use in training and clinical research purposes. These video recordings are sizable, and identified only by a patient name or number.

Abnormality detection and diagnosis decisions are made in real-time by any given physician, which are subject to that physician's visualization abilities while viewing the live video. Improvement of adenoma detection rates (ADR), a surrogate marker for endoscopic quality for colon screening consistently across physicians, is a continuing challenge.

Traditional biopsies remain the only way to objectively cross-check detection and diagnosis decisions and are extensively used to minimize chances of missing adenomas, adding several thousands of dollars of pathology costs to the overall cost of the procedure.

Ultimately, missed adenomas likely results in missed cancer detection.

Figure 9:
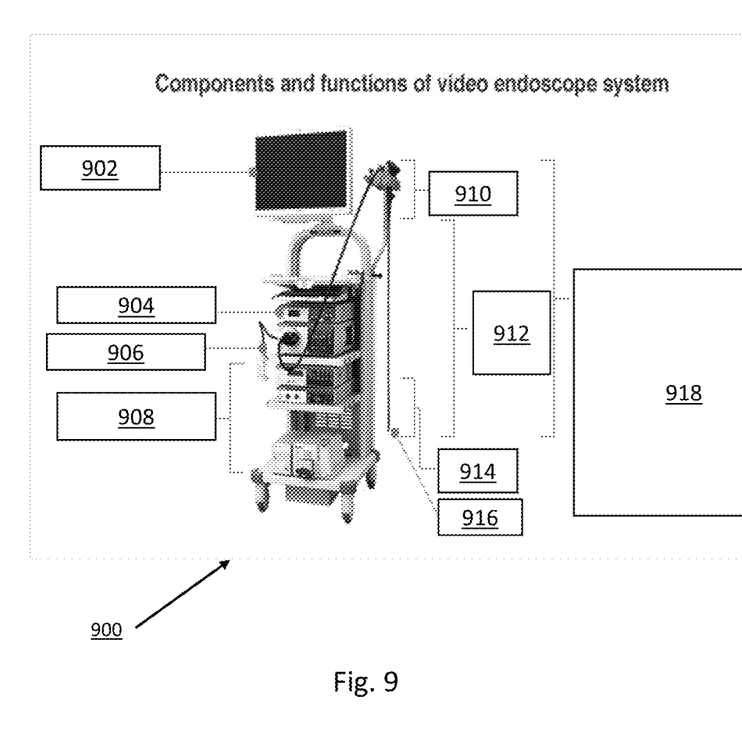
FIG. 9 shows a conventional endoscope system.

FIG. 9 shows a conventional endoscope system.

In particular, as shown in FIG. 9, an endoscope system 900 includes an LCD monitor 902, a video system center 904, a light source 906, and an image management hub and other accessories 908.

A videoscope 918 includes a control section 910, an insertion section, or shaft 912, a bending section 914, and a distal end 916. The video processor in the videoscope 918 converts electrical signals from the scope into video signals and displays them on the monitor 902. The light source 906 uses a xenon lamp to produce light similar to natural light, which is transmitted to the scope's distal end 916, and also incorporates a pump for supplying water and air to the scope 900.

Some endoscope systems (e.g., EndoChoice FUSE platform) have an inbuilt 360 degree camera, The 360 degree view eliminates blind spots but still is subject to the limitations of the expertise and experience of the physician's manual detection from the video feed. Endoscope cameras from some vendors have the capability to record at lower wavelengths for exaggeration of abnormality polyp textures.

The endoscopic video is magnified by a video processor for easier screening, detection and any necessary therapeutic/surgical action like removal of an abnormality (e.g., polyp). Video processors from some vendors can also perform certain post processing (after recording) to help with better visualization of abnormalities, e.g., tone enhancement, contrast enhancement, and specific wavelength potentiation.

Conventional endoscope systems output video to the monitor in any of a variety of proprietary and industry formats, with connection made by respective cables supporting such formats. Conventional endoscope systems output video at differing video resolutions and/or frame rates, usually dependent upon the capabilities of the endoscope system camera providing the recorded video feed.

For optimal outcome of a colonoscopy procedure, gastroenterology focused organizations recommend certain best practices. These best practices include recommendations on the amount of time spent on key aspects of the procedure (e.g., withdrawal in colonoscopy procedures), % of the procedure with a clear view of the mucosa, a number of retroflex views taken by the camera, etc.

After completion of an endoscopy procedure, a physician is expected to document their observations, findings and procedure metrics. Procedure metrics include a variety of information like length of procedure, time spent in certain parts of the digestive tract, whether certain key markers (e.g., cecum, small intestine in colonoscopy) were reached, etc. This information serves a variety of purposes, including for sharing with the patient, for billing insurance companies, and for serving as a record for future follow up. More recently this information has also started being shared with quality focused organizations like GIQuIC, which use it for benchmarking and making recommendations for improving the quality of endoscopy procedures.

Conventional endoscopy procedures are recorded to flash drives, CD-ROMs, external hard drives, etc. The proprietary nature of conventional endoscope systems often limits available storage options. Procedures often last upwards of 10 minutes and these recordings can easily run into hundreds of megabytes if not gigabytes per procedure. It is left to the physician for them to organize, label, and split recordings into clips for easier access and future use.

SUMMARY OF THE INVENTION

An endoscopy video feature enhancement platform in accordance with a first aspect of the invention includes an input video interface. A video capture device captures an input endoscopy video stream received by the input video interface. A detection module applies a previously trained detection model to the endoscopy video stream, and generates detection of a region of at least one possible abnormality in the endoscopy video stream. An abnormality identification module detects a type of the at least one possible abnormality detected by the detection module, and overlays a visual border around the detected region to generate an augmented endoscopy video stream. A video augmentation module overlays a visual indicator of the type of the at least one possible abnormality in the detected region over a relevant portion of the augmented endoscopy video stream. A video output device outputs the augmented endoscopy video stream to an output video interface.

A method of augmenting an endoscopy video feed output from an endoscope system in accordance with another aspect of the invention comprises inputting an endoscopy video stream output by an endoscope system. Images are captured from the endoscopy video stream. A previously trained detection model is applied to the endoscopy video stream. Detection of a region in the endoscopy video stream of at least one possible abnormality is generated. A type of the at least one possible abnormality in the detected region is detected. A visual border is overlaid around the detected region to generate an augmented endoscopy video stream. A visual indicator of the type of the at least one possible abnormality in the detected region is overlaid over a relevant portion of the augmented endoscopy video stream, and augmented endoscopy video stream is output to an output video interface.

A method of augmenting an endoscopy video feed output from an endoscope system in accordance with yet another aspect of the invention comprises inputting an endoscopy video stream output from an endoscope system. A picture-in-picture is detected within the input endoscopy video stream. A plurality of video clips are generated from the input endoscopy video stream each comprising image frames before and after a respective detected picture-in-picture in the input endoscopy video stream, each of the plurality of video clips spanning a given length of time. For each of the plurality of video clips, an audible prompt is output in real-time requesting a verbal finding relating to the respectively generated one of the plurality of video clips. Each responsive verbal finding is speech-to-text converted to meta data, and the meta data is associated with the respective one of the plurality of video clips.

BRIEF DESCRIPTION OF THE DRAWINGS

Features and advantages of the present invention will become apparent to those skilled in the art from the following description with reference to the drawings, in which.

DETAILED DESCRIPTION OF ILLUSTRATIVE EMBODIMENTS

Conventional endoscope systems are disadvantageous because most enhancements have heretofore been integrated into the endoscope system itself, in most cases packaged alongside other features in a proprietary system that are less beneficial or not beneficial at all to the physician. Also, because of the proprietary and closed nature of conventional implementations of feature enhancements, they are not universally available for interconnection or use on all of the various endoscope systems that a conventional endoscopy center might have, limiting choices for expansion, upgrades, improved efficiency of procedures, etc.

Furthermore, conventional endoscopy techniques are vulnerable to the possibility of oversight by the physician, with the risk of non-detection left to the expertise of the particular physician and endoscopy center staff. The prevailing view is that colorectal screening is no longer yielding much better results because of significant deviation and disparity in physician visualization capability, expertise and performance in detecting adenomas. While large abnormalities would definitely catch the attention of the eye of a manual observer, some minor/small abnormalities have a risk of going undetected because at any given moment the physician is looking at an entire big image and the presence of any minor/small abnormalities that the physician's eye is not focused upon might be left unnoticed at that moment.

The inventors hereof have appreciated that detection of some abnormalities is visually challenging. For instance, there are certain varieties of flat abnormalities that are visually occult and present a very challenging visual problem to detect them even by the most experienced eye; Especially more so during a procedure having an efficiency target of a given duration when the video frames are rapidly changing scenes while the camera wire navigates around.

The inventors hereof have also appreciated that conventional systems and techniques leave untapped the collective knowledge pool of the expertise of many endoscopy physicians using a wide variety of systems to detect the more difficult to see abnormalities. The knowledge gained from different endoscopy centers using different endoscopes is not capable of being shared on a large scale, hence resulting in some deviation and disparity in detection of abnormalities (particularly those that are more difficult to catch) across endoscopy centers on the whole.

The inventors hereof have also appreciated that there is a lack of objective real-time input or feedback with conventional endoscopes. Endoscopy centers rely mostly on the physician's expertise to interpret the live video feed. The present invention, as will be described herein below, provides physicians using all types of endoscopy systems with objective input and/or data points derived from the collective experience of a variety of different endoscopy systems. The invention overlays indicators on the output video feed of any type endoscopy system to reinforce/supplement the physician's viewpoint in real-time, to assist them in identifying features and making an 'abnormality/no abnormality' decision instantly while watching the video feed.

The inventors hereof have also appreciated that the current method of documenting endoscopy procedure findings is prone to errors, to oversight and also to unnecessarily extending the overall length of the procedure. The physician and/or assisting medical technician or nurse conventionally documents their findings from the procedure by making a mental or paper note of critical aspects and findings of the endoscopy procedure, while the procedure is in progress. They subsequently document that information electronically using procedure report writing or EMR software. A physician may typically also take image snapshots, or screenshot images, of critical aspects of an endoscopy procedure as it is performed, for inclusion in a procedure report and/or for use in future follow up of the patient. These screenshot images are conventionally automatically transferred to the procedure report using conventional procedure reporting/EMR software. Sometimes a large number of such images are captured depending upon the complexity of the procedure and associated findings. Later on, physicians often struggle to give proper context and purpose to a particular image, thereby reducing its usefulness.

The present invention, as will be described herein below, makes the image identification and documentation process efficient and accurate. The invention autonomously detects when an image snapshot has been taken by the endoscopy system and output on its output video feed, and acts on the video feed appropriately. For instance, the video feed that is output by any endoscope system is monitored by the present invention for the presence of an image snapshot (e.g., the presence of a picture-in-picture). The invention then uses the image snapshot as an indicator of a portion of the procedure that is of interest, and triggers collection of critical information for image labeling and finding documentation via verbal interaction with the physician. The invention subsequently makes that post-endoscope-system-collected data electronically available to the report writing or EMR software at the end of the procedure and prior to physician/medical technician or nurse initiating their data entry into the software.

The inventors hereof have also appreciated that while the video recordings of some key portions of an endoscopy procedure could be immensely useful in patient follow up, clinical research and training, physicians do not extensively perform and utilize these because of the time, effort and complexity to generate, store and manage these sub-recordings in a sortable and searchable manner. The present invention, as will be described herein below, generates such recordings and provides searchable meta data that makes them more useable. The invention autonomously detects when an image snapshot has been taken on the incoming video feed (an indicator of portion of procedure of interest) and triggers automatic generation of short procedure video clips around those areas of interest. The invention also makes input collected from physician as meta data and tags for the clips generated, thereby making the recordings more useable, sortable and searchable on basis of them.

Figure 1:
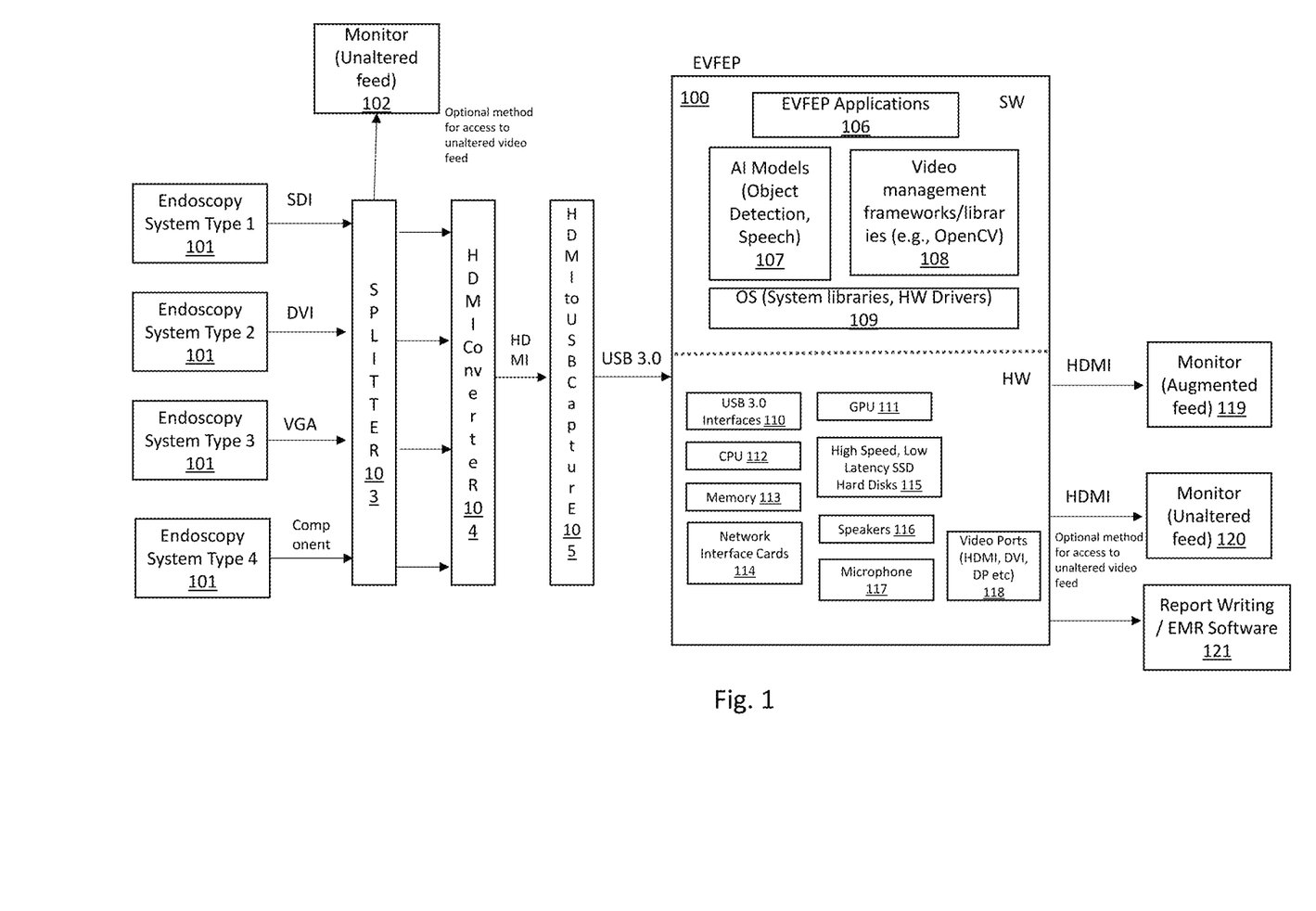
FIG. 1 shows a high-level contextual view of an endoscopy video feature enhancement platform (EVFEP) connected to the output of an existing endoscope system infrastructure, to provide an enhanced set of video features for use with any type endoscope system, in accordance with the present invention.

FIG. 1 shows a high-level contextual view of an endoscopy video feature enhancement platform (EVFEP) 100 connected to the output of an existing endoscope system infrastructure, to provide an enhanced set of video features for use with any type endoscope system, in accordance with the present invention.

As shown in FIG. 1, on top of conventional fixed video features integrated into a particular vendor's proprietary endoscope system, the invention provides an endoscopy video feature enhancement platform (EVFEP) 100 connected external to the output of the proprietary endoscope system, i.e., to a video feed output from the endoscope system.

The endoscopy video feature enhancement platform (EVFEP) 100 includes hardware and software required to support external feature functionality and performance. The EVFEP includes a set of EVFEP applications 106, which in conjunction with Artificial Intelligence software 107 models trained on relevant images and speech, video management framework and libraries 108, and operating system libraries and drivers 109 provide universal feature enhancements to the output from any type endoscope system during an endoscopy procedure.

Disclosed embodiments include high speed USB 3.0 interfaces 110 for connecting to incoming endoscopy video feed, output video ports 118 for connecting to up to two monitors: a first monitor 119 for display of augmented video and another monitor 120 for display of video passed through unaltered.

Hardware used by the endoscopy video feature enhancement platform 100 also includes a CPU 112 and memory 113 for running the EVFEP applications 106, speakers 116 and a microphone 117 for verbal interaction with the physician, network interface cards 114 for interfacing with a reporting system 121 such as Report Write/EMR, high speed SSD disks 115 for storage of procedure video recordings without impacting performance, and GPU(s) 111 for high speed AI model processing and video rendering from images without discernable latency.

The endoscopy video feature enhancement platform 100 connects to the output of existing different endoscope systems 101, whether or not the endoscope system includes its own integrated, proprietary video enhancement features.

Between the different endoscope systems 101 and the endoscopy video feature enhancement platform 100 are video switches or splitters 103, HDMI video converters 104, and HDMI to USB video capture adapters 105, depending upon the model and capability of the different endoscope systems 101 and the types of video capabilities they have. One or more monitors may optionally be connected to the video switch/splitter 103 for viewing the unaltered video output from any or all of the different endoscope systems 101.

Figure 2:
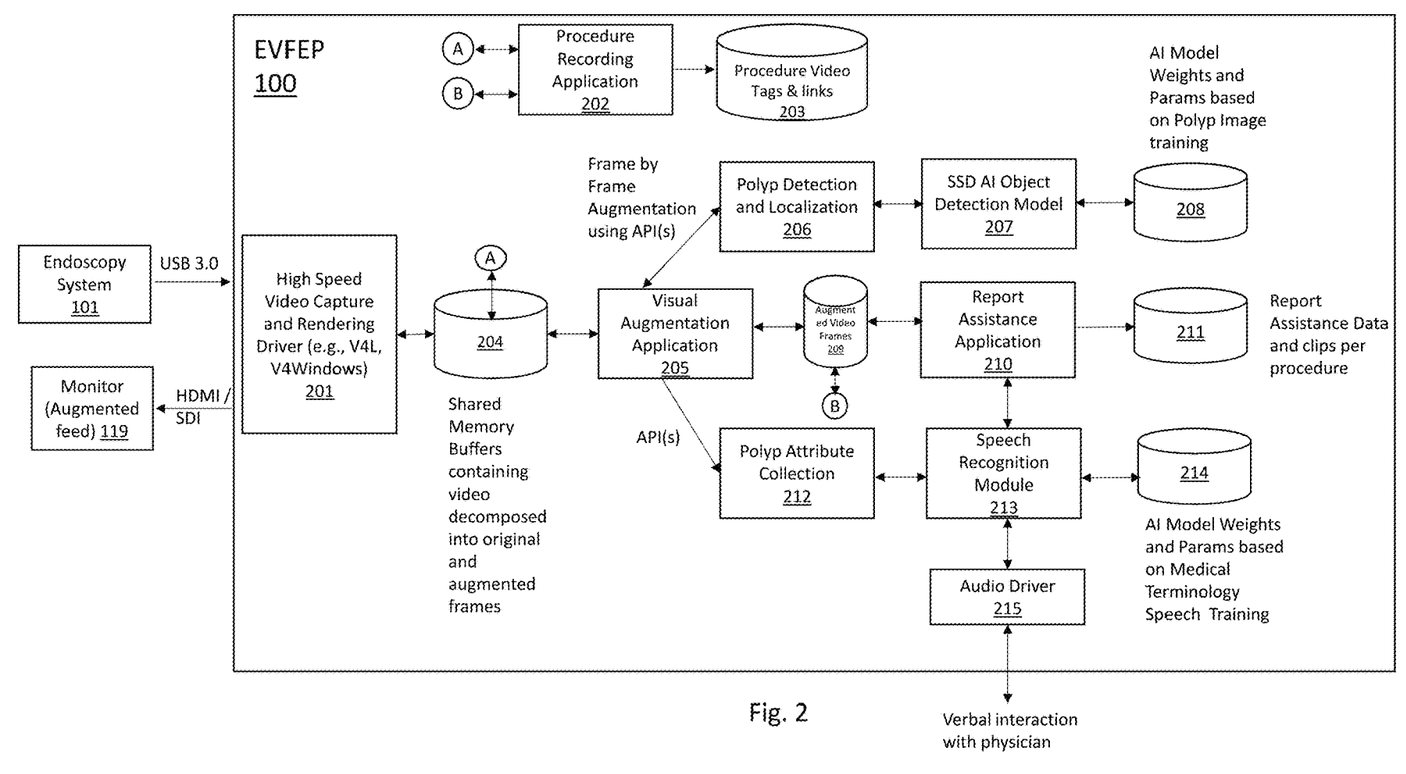
FIG. 2 shows a decomposition of an endoscopy video feature enhancement platform (EVFEP), in accordance with embodiments of the invention.

FIG. 2 shows a decomposition of an endoscopy video feature enhancement platform (EVFEP), in accordance with embodiments of the invention.

In particular, as shown in FIG. 2, the EVFEP includes a high speed video capture and rendering driver (e.g., V4L, V4Windows) 201 to receive the video feed output from any endoscope system 101, and to output an augmented video feed output to a monitor 119 for the physician to refer to visually. The endoscopy video feature enhancement platform 100 first processes an incoming video signal output from an endoscope system 101. In disclosed embodiments the video signal is input to the endoscopy video feature enhancement platform 100 over a USB 3.0 interface 110 using appropriate software drivers 201 packaged with operating systems (e.g., V4L in Linux) for real-time high-speed video capture and rendering. The drivers 201 capture video at a configured frame rate (30 or 50 fps typically when connected to the output of an endoscope system 101) and transfers decomposed video in the form of image by image to a visual augmentation application 205 via shared memory buffers 204.

The video incoming and outgoing to the EVFEP 100 is buffered in a suitable data storage area 204. The shared memory buffers 204 contain video decomposed into original and augmented frames.

The visual augmentation application 205 operates at frame/image level and performs various forms of augmentation (polyp detection and localization, adding of polyp attributes and procedure metrics). The visual augmentation application 205 interfaces with a polyp detection and localization module 206 using pre-defined API(s) for frame/image by frame/image augmentation.

The polyp detection and localization module 206 uses a single shot deep convolution neural network artificial intelligence object detection model 207 for detecting and localizing the polyps.

The deep convolution neural network single shot artificial intelligence object detection model 207 uses model weights and parameters 208 that are generated from previous training. The previous training is preferably updated periodically or from time to time, as the confirmed results of endoscopy procedures on a large scale from many different types of endoscope systems are included in the artificial intelligence training. Preferably the training includes use of confirmed detection of hundreds of thousands of images showing polyps with different morphology and in different areas of the colon extracted from hundreds of thousands of video recordings of endoscopy procedures output from many different endoscope systems. The detection results in the video recordings are confirmed by expert gastroenterologists as they perform the respective endoscopy procedures, thus enabling the benefit of the collective experiences and decisions and best practices followed by other gastroenterologists—no matter what type endoscope system is used for the procedure. The single shot model which performs localization and classification in a single step is chosen for its real-time performance which is critical to providing this capability without addition of discernable latency.

The visual augmentation application 205 also connects with a polyp attribute collection module 212 using pre-defined API(s) for populating certain polyp attributes.

The polyp attribute collection module 212 uses a speech recognition module 213 for collecting verbal input from physicians for assisting with polyp attribute generation.

The speech recognition module 213 which includes a deep convolution neural network artificial intelligence model uses model weights and parameters 214 that were generated from previous training on hundreds of thousands of commonly used medical words that are expected to be used while collecting verbal input from physicians.

The speech recognition module 213 interfaces with audio drivers 215 using pre-defined API(s) for verbal interaction with the physician.

After completing all types of frame augmentation, the visual augmentation application 205 passes on the augmented frames to a report assistance application 210 for further processing via shared memory buffers 209. These frames are also marked if they contain a picture-in-picture frame for special processing within this application related to generating clips of interest.

The report assistance application 210 aggregates the information including tags and links to clips for sharing with the reporting system (e.g., Report Writing/EMR software) in a separate database 211. The clips and associated tags can also be utilized for other purposes like clinical research.

At shared memory buffers 204 and 209 before and after visual augmentation application 205 respectively, there is an option to generate a procedure recording by a procedure recording application 202. SSD hard disks 115 are used for fast disk writes. The recording is done via a separate software thread so as not to block or delay other processing happening in the EVFEP 100. The recording can be done in anonymized or non-anonymized mode. In anonymized mode, the filename is made unique by embedding the data and time of the procedure. In anonymized mode, the physician can enter the name of the patient while enabling recording for the procedure.

The procedure recording application 202 stores in database 203 the meta data and tags associated with each procedure collected during image augmentation for augmented video recording. This database 203 also contains links to where the procedure recordings are stored.

For re-rendering and outputting the video over different video interfaces, the augmented/modified images are transferred by the visual augmentation application 205 to software drivers 201 via shared memory buffers 204.

The visual augmentation application 205 on the EVFEP 100 provides following capabilities—Polyp Detection & localization, Polyp Characterization and Procedure Metrics in each video frame 300.

Figure 3:
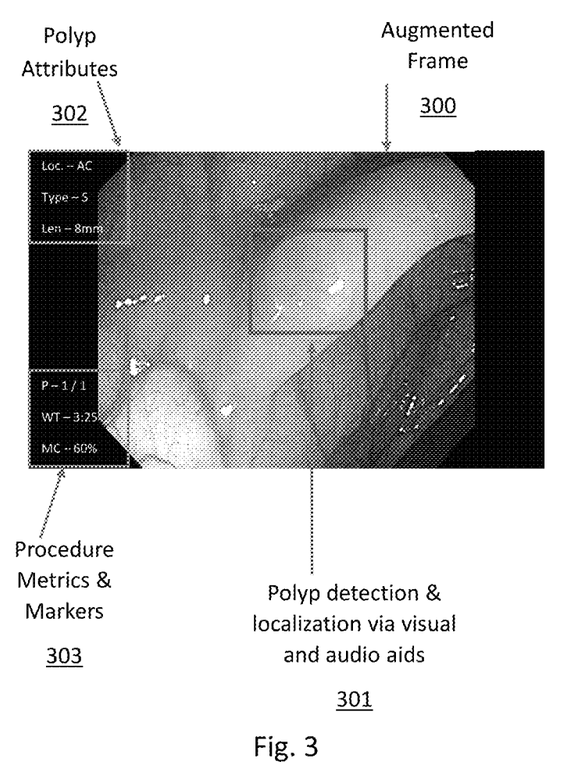
FIG. 3 shows an exemplary visual augmentation of a colonoscopy video with automated polyp detection and augmented reality overlay detail, in accordance with the principles of the present invention.

FIG. 3 shows an exemplary visual augmentation of a colonoscopy video with automated polyp detection and augmented reality overlay detail, in accordance with the principles of the present invention.

In particular, to reduce oversights, the polyp detection and localization module 206 also preferably visually bounds the abnormality with a rectangular bounding box 301 as seen in FIG. 3, so as to immediately catch the physician's eye, letting them know to zoom-in to explore that region in more detail, or that the area may be ignored as a likely false positive. This enables the physician to make an informed decision and to reduce oversights. If configured, this module 206 could also provide audio alerts to catch physician's attention.

Polyp attribute collection module 212 provides the size, location and morphology type of the polyp. The Polyp attribute information 302 is displayed on top left corner area of the screen as seen in FIG. 3. It is displayed only when a polyp (or possible polyp) has been noted and is being removed. The polyp location within colon (sigmoid, ascending, descending, transversal, etc.) and morphology type (sessile, flat, pedunculated) are additional outputs of the SSD AI object detection model 207 discussed above. The polyp size is determined by comparison with reference object of known size. The reference object in this case is the instrument used for its removal, which is visible simultaneously with the polyp just prior to its removal. The real size of the instrument is known a priori.

The procedure metric information 303 is displayed on bottom left corner of the screen as seen in FIG. 3. It provides the number of polyps detected and removed, clear mucosal coverage percentage and withdrawal time. Once the polyp is detected it can remain visible on the video for extended period of time and the same is true of the polyp removal as well. Hence it is not easy to count the polyps detected and removed autonomously.

Figure 4:
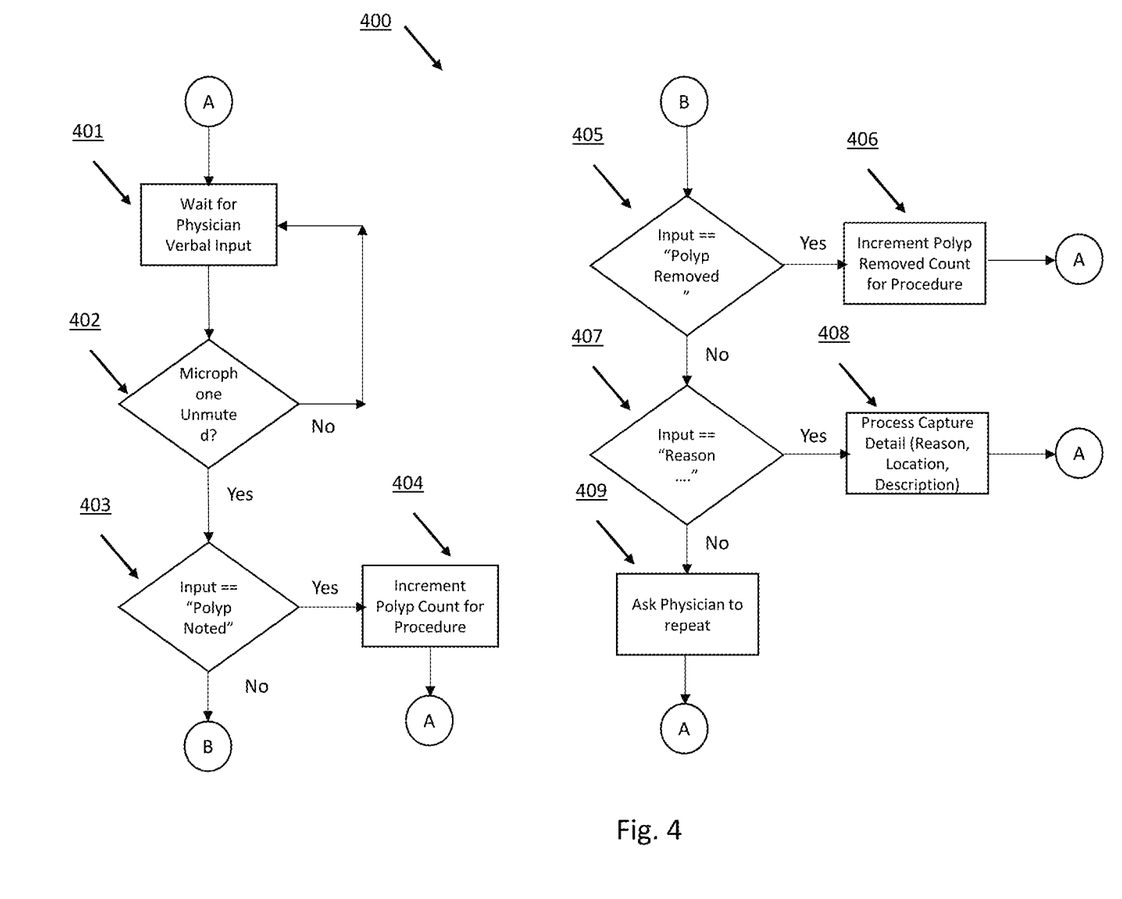
FIG. 4 shows an exemplary speech recognition process flow for counting polyps noted, removed image capture processing.

FIG. 4 shows an exemplary speech recognition process 400 for counting polyps noted, removed image capture processing.

In particular, as shown in FIG. 4, polyp count for detection and removal is made with the assistance of physician verbal input.

The exemplary speech recognition process 400 preferably begins at process block 401, waiting for verbal input from physician. Periodical evaluation 402 may be made to determine whether or not the microphone has been unmuted. Following unmuting of the microphone, the collected verbal input from physician is interpreted and compared with different phrases.

For instance, if the collected verbal input is determined to be "polyp noted" as shown in step 403, the polyp count for the procedure is incremented in step 404.

In step 405, if the collected verbal input is determined to be "polyp removed", the polyp removed count for the procedure is incremented in step 406.

In step 407, if the collected verbal input is determined to be, e.g., "reason" followed by a comment, the process captures detail dictated by the physician, e.g., reason, location, description, etc., as shown in step 408.

If no matches are noticed, the physician may be asked to repeat at step 409 by output of a signal to the physician to the speakers 116. The interpretation utilizes speech recognition AI model 213 specifically trained to recognize and interpret medically focused word set to be used by the physicians while performing the procedures. Unlike voice assistants (e.g., Alexa, Google Home etc.) where the microphone is constantly is listen mode, verbal communication with EVFEP is initiated by explicitly turning the microphone 117 on by the physician. This alleviates patient and physician privacy issues.

Successful evaluation at step 403 against phrase "Polyp Noted" increments procedure polyp observed count by module 404.

Successful evaluation at step 405 against phrase "Polyp Removed" increments procedure polyp removed count at step 406.

Successful evaluation at step 407 against phrase "Capture Reason" triggers processing as per step 408 for benefit of report assistance application 210.

Clear Mucosal Coverage percentage is determined by dividing the percentage of non-blurred frames to the total frames observed during the procedure.

The withdrawal time preferably starts a count from the time cecum is observed by the physician and the physician starts withdrawing the camera from the colon. Detection and localization of cecum is also and additional output of the SSD AI object detection model 207.

Currently physicians capture images of key aspects of the procedure using built in capabilities and integration of their endoscope system and procedure reporting software. The image capture coincides with a picture-in-picture appearance on the video output from the endoscope system which captures the image taken.

Figure 5:
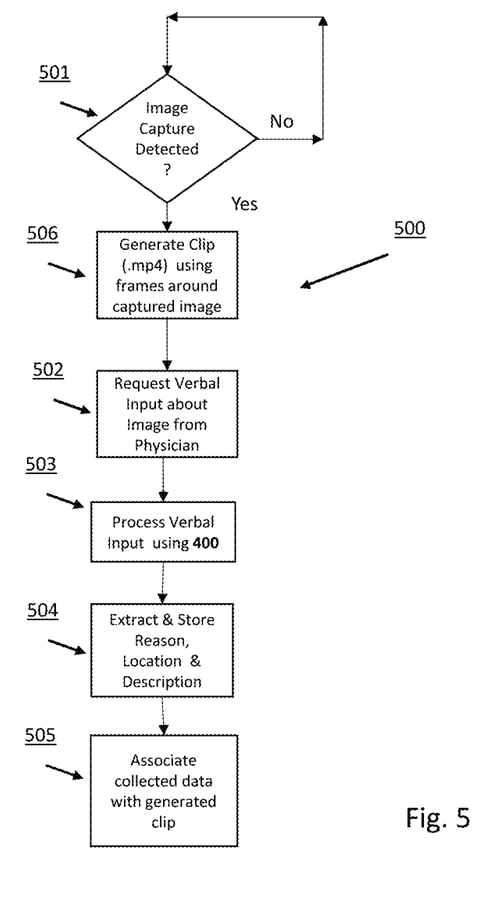
FIG. 5 shows exemplary process flow for automatic detection of such image capture in the endoscope system to trigger post-output generation of a short video clip using frames around that image and verbal interaction with a physician to collect tags and meta data that are associated with those images and clips.

FIG. 5 shows exemplary process flow 500 for automatic detection of such image capture in the endoscope system to trigger post-output generation of a short video clip using frames around that image and verbal interaction with a physician to collect tags and meta data that are associated with those images and clips.

In particular, as shown in step 501 of FIG. 5, image capture is detected in the output video feed of any type endoscope system and used as an indicator of an area of interest within the procedure.

In step 506, clip generation is automatically triggered from the incoming endoscopy video feed upon the detection of an image capture.

In step 502, verbal input about the image is requested from the physician.

In step 503, verbal input is received and processed using the speech recognition process 400.

In step 504, the spoken reason, location and description and any other information verbally provided by the physician are extracted and stored as text in meta data. The meta data is associated in step 505 with the triggered clip generated in step 506.

The process flow 500 implemented within the report assistance application 210 preferably evaluates for image in image in the incoming video feed (output from any type endoscope system), an indicator of image capture by physician using process block 501. If the evaluation is successful, the process flow 506 automatically generates short video clips by aggregating pre-configured number of frames before and after the image. Each video clip generated in this manner has a unique filename which preferably includes a procedure identifier provided by the physician and a clip sequence number. The process flow 500 also collects input from the physician using process block 502 for use as meta data for these clips as well as for assisting with procedure documentation later. The process block 502 may use speakers 116 for this purpose. The verbal input is collected by a microphone, evaluated and processed using speech recognition process 400 (FIG. 4). The verbal input for this particular is collected by process block 408 and passed along to process block 503 for further processing and extracted by process block 504. This information includes the purpose of image/clip capture, location within colon and additional description. A sample input could be "Reason Biopsy, Location Ascending Colon, Description Colitis". This information is stored in a separate data file of the format 600 that can be easily associated to the captured image, clips and the procedure.

Figure 6:
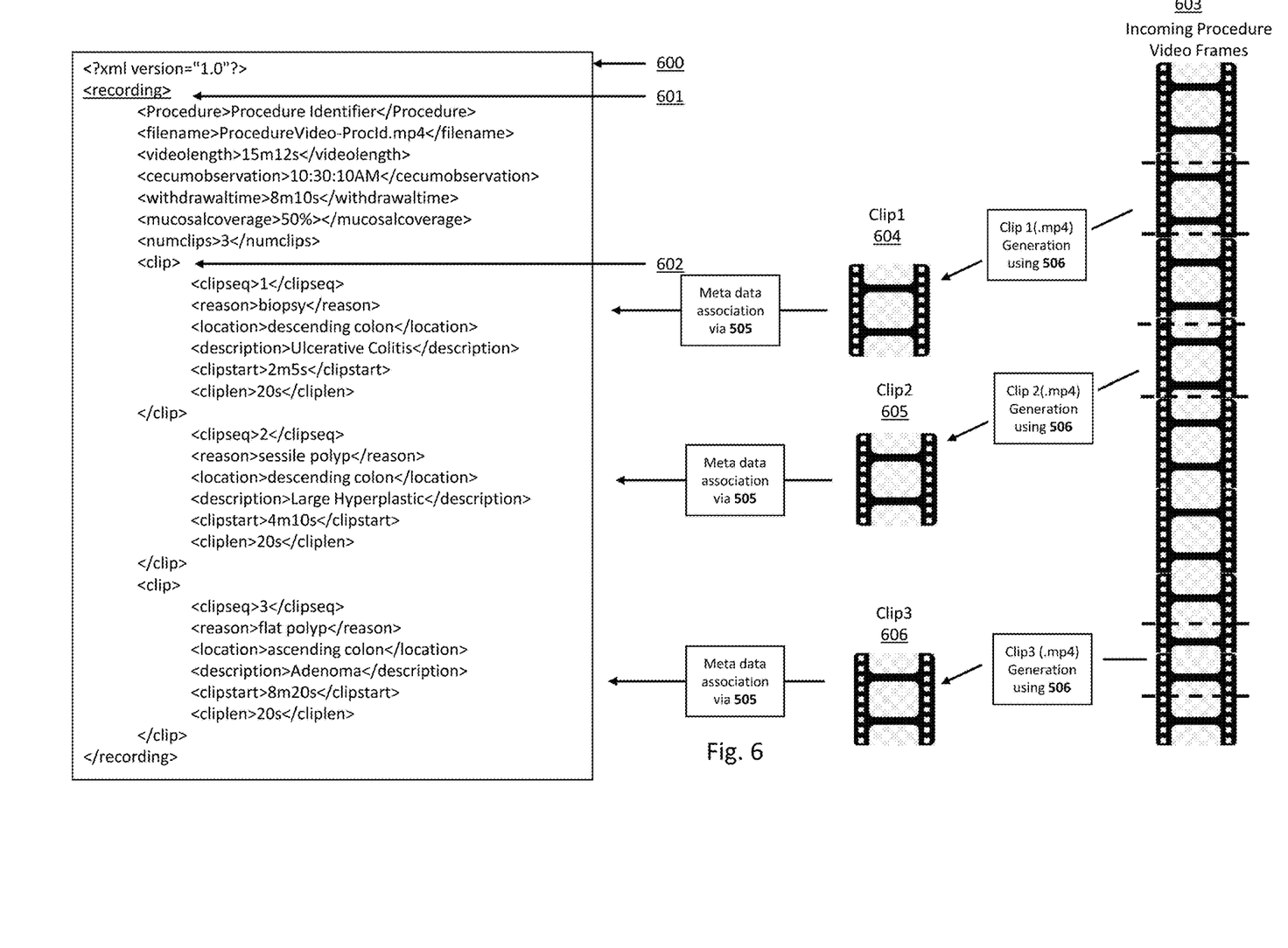
FIG. 6 shows a sample aggregated data record aggregated by an EVFEP for assisting with procedure report generation and clip tagging.

FIG. 6 shows a sample aggregated data record 600 aggregated by an EVFEP for assisting with procedure report generation and clip tagging.

In particular, the figure also shows how clips 604, 605 and 606 are generated using a sequence of video frames before and after the detected captured image in the incoming video feed (output from any type endoscope system) and how the data associated with these clips maps to a clip associated portion 602 of a data record 600. The remote assistance application 210 within the EVFEP 100 also aggregates related to polyp finding and procedure metric—Polyp Finding, Cecum Observation Time, Withdrawal Time, Clear Mucosal Coverage and includes them in portion 601 of the data record 600.

The report assistance application 210 within the EVFEP 100 (FIG. 2) also shares this procedure information with reporting software or EMR software for generating procedure documentation. At the completion of the procedure, the report assistance application 210 electronically communicates this to the procedure reporting software or EMR software to minimize manual input by physician. The electronic transfer mode will vary depending upon capabilities and agreements with the vendors of the above software and could include file transfer or communication between the two software applications using pre-defined APIs.

Figure 7:
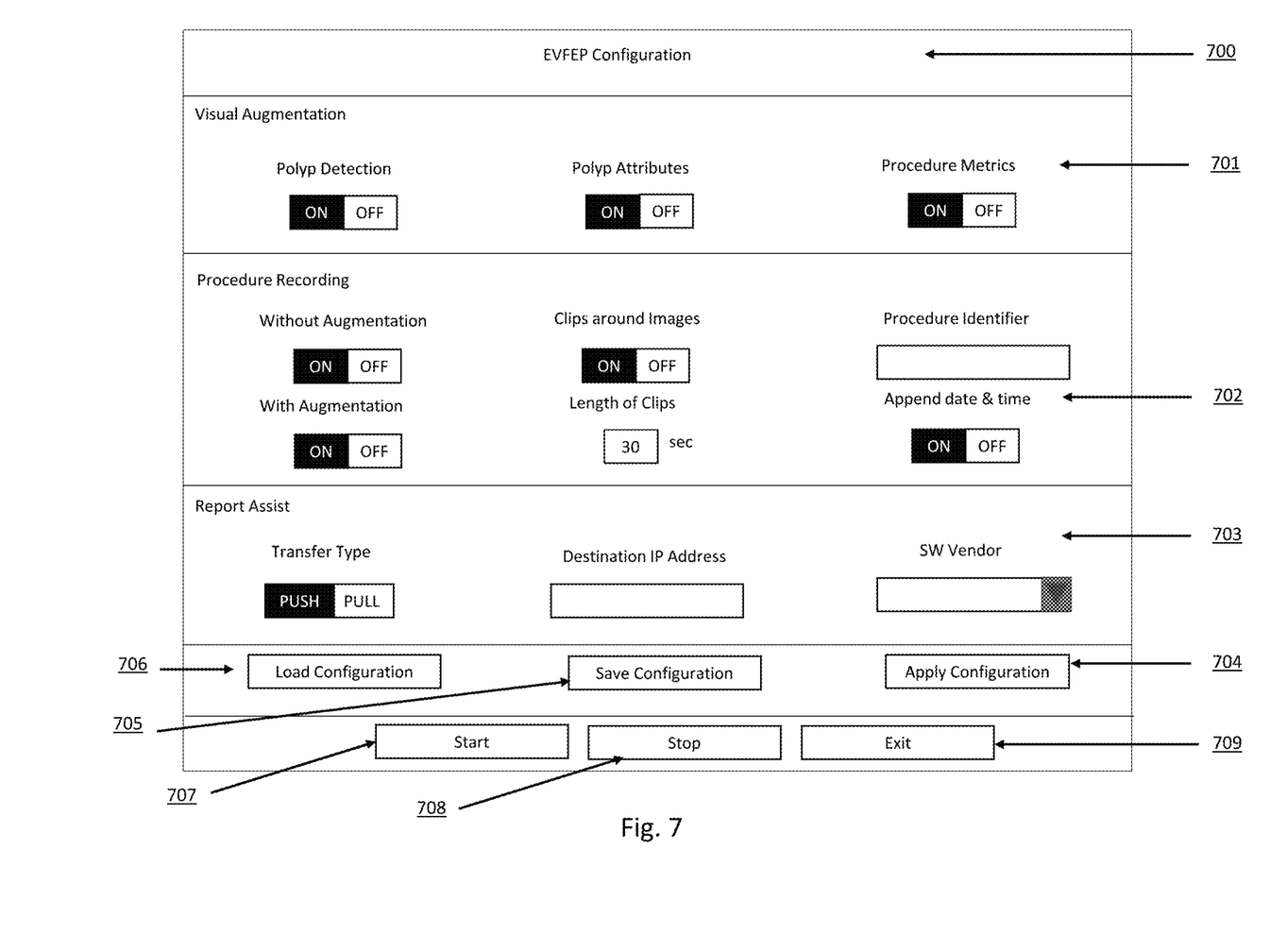
FIG. 7 shows a sample configuration screen for an endoscopy video feature enhancement platform (EVFEP), in accordance with the invention.

FIG. 7 shows a sample configuration screen for an endoscopy video feature enhancement platform (EVFEP), in accordance with the invention.

In particular, upon activation of the EVFEP 100 a configuration screen 700 is presented to the physician to determine which applications are to be enabled. The configuration settings can be stored in a default profile to eliminate the need of unnecessary configuration at the start of each procedure if the settings are expected to be the same across different procedures. The real-time processing of procedure video can be started or stopped using screen as well.

The SSD AI object detection model 207 and the speech recognition module 213 within the EVFEP 100 can be updated for general performance improvements or performance improvements optimized for specific endoscope system manufacturer or model or another language or dialect just by uploading different set of model weights and hyper-parameters 208 and 214 based on polyp image training respectively and without any change in model software.

The invention provides for improved training of new fellows, physicians, technicians new to the field.

The invention has particular application with endoscopy centers, ambulatory surgery centers, and hospitals. The invention also has applicability with gastroenterologist physicians for esophagogastroduodenoscopy, and may be adapted for use in other specialties such as Urology, Gynecology that use endoscope systems.

The video feature enhancement platform (EVFEP) 100 is capable of generating various metrics and statistics related to processing functions of a variety of different types of endoscope systems, compiled, and utilized afterwards for analytical processing.

The above Detailed Description of embodiments is not intended to be exhaustive or to limit the disclosure to the precise form disclosed above. While specific embodiments of, and examples are described above for illustrative purposes, various equivalent modifications are possible within the scope of the system, as those skilled in the art will recognize. For example, while processes or blocks are presented in a given order, alternative embodiments may perform routines having operations, or employ systems having blocks, in a different order, and some processes or blocks may be deleted, moved, added, subdivided, combined, and/or modified. While processes or blocks are at times shown as being performed in series, these processes or blocks may instead be performed in parallel, or may be performed at different times. Further, any specific numbers noted herein are only examples; alternative implementations may employ differing values or ranges.

Unless the context clearly requires otherwise, throughout the description and the claims, references are made herein to routines, subroutines, and modules. Generally it should be understood that a routine is a software program executed by computer hardware and that a subroutine is a software program executed within another routine. However, routines discussed herein may be executed within another routine and subroutines may be executed independently, i.e., routines may be subroutines and vice versa. As used herein, the term "module" (or "logic") may refer to, be part of, or include an Application Specific Integrated Circuit (ASIC), a System on a Chip (SoC), an electronic circuit, a programmed programmable circuit (such as, Field Programmable Gate Array (FPGA)), a processor (shared, dedicated, or group) and/or memory (shared, dedicated, or group) or in another computer hardware component or device that execute one or more software or firmware programs or routines having executable machine instructions (generated from an assembler and/or a compiler) or a combination, a combinational logic circuit, and/or other suitable components with logic that provide the described functionality. Modules may be distinct and independent components integrated by sharing or passing data, or the modules may be subcomponents of a single module, or be split among several modules. The components may be processes running on, or implemented on, a single computer, processor or controller node or distributed among a plurality of computer, processor or controller nodes running in parallel, concurrently, sequentially or a combination.

While the invention has been described with reference to the exemplary embodiments thereof, those skilled in the art will be able to make various modifications to the described embodiments of the invention without departing from the true spirit and scope of the invention.

What is claimed is:

1. An endoscopy video feature enhancement platform, comprising:
   an input video interface to input an unaugmented mirrored monitor video stream output from an endoscopy system directly through a mirrored part on the endoscopy system;
   a digital video splitter to digitally split the input unaugmented mirrored monitor video stream into both an unaugmented mirrored monitor video stream for output to an unaugmented video interface, and a mirrored endoscopy video stream for post-endoscopy-system real-time augmentation;
   a detection module to apply in real time a previously trained detection model to the mirrored endoscopy video stream, and generate in real time detection of a region of at least one possible abnormality in a subject patient shown in a relevant portion of the mirrored endoscopy video stream;
   an abnormality attribute collection module to determine in real time at least one attribute of the at least one possible abnormality generated by the detection module, to overlay in real time a visual border around the detected region within each frame including the detected region, and to overlay in real time the at least one attribute of the at least one possible abnormality within each said frame, of the relevant portion of the mirrored endoscopy video stream, to generate an augmented endoscopy video stream;
   a video augmentation module to overlay in real time, within each said frame of the augmented endoscopy video stream including the visual border around the detected region, a visual indicator of a location of the at least one possible abnormality within each said frame, and the at least one attribute of the at least one possible abnormality;
   an output video interface; and
   a video output device to output the augmented endoscopy video stream to the output video interface.

2. The endoscopy video feature enhancement platform according to claim 1, wherein:

the input video interface is a Universal Serial Bus interface.

3. The endoscopy video feature enhancement platform according to claim 1, wherein:
the output video interface is an HDMI output.

4. The endoscopy video feature enhancement platform according to claim 1, further comprising:
a video converter to convert a first video format of the input unaugmented mirrored monitor video stream to a different, second video format.

5. The endoscopy video feature enhancement platform according to claim 1, wherein:
the video augmentation module further overlays on the augmented endoscopy video stream textual information relating to the at least one attribute of the at least one possible abnormality.

6. A method of augmenting an endoscopy video feed output from an endoscope system, comprising:
inputting an unaugmented mirrored monitor video stream output from an endoscopy system directly through a mirrored part on the endoscopy system or optionally through a digital video splitter;
digitally splitting the input unaugmented mirrored monitor video stream into both an unaugmented mirrored monitor video stream for output to an unaugmented video interface, and a mirrored endoscopy video stream for post-endoscopy-system real-time augmentation;
applying in real time a previously trained detection model to the mirrored endoscopy video stream;
generating in real time detection of a region of at least one possible abnormality in a subject patient shown in a relevant portion of the mirrored endoscopy video stream;
determining in real time at least one attribute of the at least one possible abnormality in the detected region;
overlaying in real time a visual border around the detected region within each frame including the detected region, and to overlay in real time the at least one attribute of the at least one possible abnormality within each said frame, of the relevant portion of the mirrored endoscopy video stream, to generate an augmented endoscopy video stream;
overlaying in real time, within each said frame of the augmented endoscopy video stream including the visual border around the detected region, a visual indicator of a location of the at least one possible abnormality within each said frame, and the at least one attribute of the at least one possible abnormality; and
outputting the augmented endoscopy video stream to an output video interface.

7. The method of augmenting an endoscopy video feed output from an endoscope system according to claim 6, further comprising:
converting a first video format of the input unaugmented mirrored monitor video stream to a different, second video format.

8. The method of augmenting an endoscopy video feed output from an endoscope system according to claim 6, further comprising:
overlaying in real time on the augmented endoscopy video stream textual information relating to the at least one attribute of the at least one possible abnormality.

9. The method of augmenting an endoscopy video feed output from an endoscope system according to claim 6, wherein:
the input unaugmented mirrored monitor video stream output by the endoscopy system is already enhanced by the endoscope system.

10. The method of augmenting an endoscopy video feed output from an endoscope system according to claim 6, further comprising:
periodically updating the trained detection model with a new detection model trained on additional endoscopy results.

11. An endoscopy video feature enhancement platform, comprising:
an input video interface to input an unaugmented mirrored monitor video stream output from an endoscopy system directly through a digital video splitter to digitally split the input unaugmented mirrored monitor video stream into both an unaugmented mirrored monitor video stream for output to an unaugmented video interface, and a mirrored endoscopy video stream for post-endoscopy-system real-time augmentation;
a detection module to apply in real time a previously trained detection model to the mirrored endoscopy video stream, and generate in real time detection of a region of at least one possible abnormality in a subject patient shown in a relevant portion of the mirrored endoscopy video stream;
an abnormality attribute collection module to determine in real time at least one attribute of the at least one possible abnormality generated by the detection module, to overlay in real time a visual border around the detected region within each frame including the detected region, and to overlay in real time the at least one attribute of the at least one possible abnormality within each said frame, of the relevant portion of the mirrored endoscopy video stream, to generate an augmented endoscopy video stream;
a video augmentation module to overlay in real time, within each said frame of the augmented endoscopy video stream including the visual border around the detected region, a visual indicator of a location of the at least one possible abnormality within each said frame, and the at least one attribute of the at least one possible abnormality;
an output video interface; and
a video output device to output the augmented endoscopy video stream to the output video interface.

* * * * *